United States Patent [19]

Yale

[11] 4,202,331
[45] May 13, 1980

[54] SKIN GRAFT PRESSURE PAD

[76] Inventor: William S. Yale, 215 E. Chicago, Chicago, Ill. 60611

[21] Appl. No.: 821,621

[22] Filed: Aug. 3, 1977

[51] Int. Cl.$^2$ ............................................. A61F 13/00
[52] U.S. Cl. .................................... 128/155; 128/1 R
[58] Field of Search ............... 128/155, 325, 327, 258, 128/379, 399, 400, 402

[56] References Cited

U.S. PATENT DOCUMENTS

| | | | |
|---|---|---|---|
| 783,827 | 2/1905 | Gasaway et al. | 128/258 X |
| 1,025,012 | 4/1912 | Norwood | 128/258 X |
| 1,238,901 | 9/1917 | Ferguson | 128/258 X |
| 3,171,410 | 3/1965 | Towle, Jr. et al. | 128/155 |

OTHER PUBLICATIONS

"Pressure Bags for Skin Grafting" Sug. Gynec. & Obst. vol. 43, p. 99, 1926.

Primary Examiner—John D. Yasko
Attorney, Agent, or Firm—Jacques M. Dulin

[57] ABSTRACT

Apparatus and method for applying more uniform pressure to an area of skin that is undergoing a skin graft. Pressure pad comprises a soft, pliable, transparent plastic envelope fillable with a viscous, transparent liquid to provide even distribution of pressure while permitting visual inspection of, and transmission of radiation to bathe the skin graft area, without removal of the pressure pad. Pad is removably securable to the area adjacent the graft by a variety of securing means. In one embodiment the graft area contact surface of the pad is specially adapted to permit air to contact the graft tissue. Pad is sterilizable, and the envelope is of a nature that drying tissue and serous fluid will not adhere to it. Pad preferably has a port permitting precise control of the amount of liquid fill (preferably silicone) in the bag, introduced or withdrawn by means of a syringe. In turn, this permits precise control of the pressure applied to the graft tissue. Pad structure is adapted to be highly conformable to irregular surface contours insuring full contact and uniform hydrostatic pressure on graft tissue.

19 Claims, 4 Drawing Figures

SKIN GRAFT PRESSURE PAD

FIELD OF THE INVENTION

This invention relates to skin grafting apparatus and methods, and more particularly to the problem of promoting contact between graft tissue and host tissue so that the graft will take with minimum necrosis. Special liquid-fillable pressure pads and methods provide necessary pressure, are disposable or non-disposable and sterilizable, and permit precise placement and control thereof. Use procedure is easy and faster than present methods.

BACKGROUND

A problem in the field of skin grafting is the difficulty of keeping the entire area of the skin to be grafted in uniform contact with the host tissue beneath it. If even a small portion of the skin being grafted does not make proper contact with the underlying tissue, that portion can die within 48 hours. The loss area must then cover itself over by ingrowth from surrounding graft tissue that has taken. The possibilities of unnecessary scarring, and infection increase, and the entire grafting process is lengthened. While uniform skin to host contact is recognized as necessary, it has not been achieved with 100% consistency in areas involving skin motion (even though splinted) or in areas of irregular contour (such as on fingers, nose, and ears).

The most common and almost universal present-day technique of promoting uniform skin graft contact consists of tying a stent, made of left-over pieces of gauze found on the nurse's Mayo stand, over the area being grafted. As these are not designed for the purpose and ill serve it, surgeons wet the stent before cutting it to the shape of the grafted area. Others try wadded cotton wet with water or mineral oil. For a convex area, some surgeons use very stiff, large-mesh gauze. The makeshift stent is then tied over by sutures along the margin of the graft. This is a time-consuming procedure, and results in a spider web of dozens of ties along the ends of the dressing. It usually requires two persons to make the ties.

These present-day make-shift stents have ragged ends with threads and lint hanging over the ends. It is difficult to apply even pressure in small areas. The sutures usually loosen after a few days, lessening the needed pressure on the graft. Of course, excess pressure will prevent proper circulation of the graft tissue from the host and will result in slow grafting or tissue necrosis. This is typically the case in raised areas, e.g. the dorsum of the nose, where uneven, excess pressure causes sloughing. Likewise, in many instances an edge of a graft is lost because the make-shift stent did not apply even pressure at the margin.

Between the second and fifth post-operative day, some surgeons disrupt a portion of the stent to view the viability of the graft tissue or the accumulation of pus. Since the stent is opaque and only one edge is viewed, surgeons presently conclude by inference that if the one corner is good, the whole graft has survived. This often proves a false inference due to the nature of the gauze stents and tying procedures.

Another serious problem is adherence of graft tissue to the stents. Numerous materials, such as saline-soaked or mineral oil-soaked gauze, "Xeroform" brand gauze, Owin's gauze, Bacitracin or Neomycin-impregnated 4×4's and "Adaptic" brand sheets, have been placed over the graft to attempt to prevent adherence and tearing-off of the graft at the time of stent removal. No one present method is perfectly free of this adherence problem, and a great deal of time and soaking of stents is employed to aid their removal.

In the past, pneumatic splints or wound dressings have been provided. For example, U.S. Pat. No. 3,171,410 discloses an oval shaped (in cross-section) inflatable bladder having a gauze pad on the side facing the wound. Pressure-sensitive tape passes over the other side of the bladder and extends therebeyond to secure the bladder to the recipient (injury) site. The bladder is filled with air or gas at a high pressure, sufficient to control bleeding. Because of the oval cross section, the wound-facing side of the gas-inflated bladder is convex. This means that the bladder edges will not contact the skin surface, unless excessive pressure is placed on the assembly. Such gas-inflated structures are prone to gradual leaking of gas at the valve. To my knowledge, surgeons have not used this assembly for grafting, and it does not appear well suited to solving the grafting problems described above.

Lehmann and Hay developed an air-inflated polyvinyl plastic sheath for the arm and leg as a pressure dressing for skin grafting; Lehmann, A. L. and Hay, L. J., "A Controlled Pressure Plastic Dressing for Skin Grafting, Burns, and Thrombophlebitis," Surgery, March 1954, Vol 15, No. 3, pp 401–404. Similarly, Smith, in a short note entitled "Pressure Bags for Skin Grafting" Sug. Gynec & Obst., Vol 43, p 99 (1926) describes relatively thick, opaque, rubber, air-inflated bags of various shapes and sizes to furnish pressure dressings for Wolfe grafts. These bags are placed over a sterile vessel (probably a gauze or cotton stent) covering the graft, fixed lightly with either a gauze or lint bandage supported by adhesive tape, and inflated to a pressure of 33 mm Hg. On the 4th day the bag is deflated and the dressing opened to care for blebs or small pustules in the graft. Care must be taken not to disturb the graft in any way. The entire dressing is replaced. One design is for a nose bag, which includes an upper and lower tube for passing hot or cold water therethrough, thereby heating or cooling the graft. Schwager, R. G., and Imber, G. in "Inflatable Splint To Immobilize Extremities After Skin Grafting," Plastic and Reconstructive Surgery J., Vol 57, No. 4, p 523 April, 1976 describe the use of inflatable spints applied over traditional gauze dressing. The skin grafts are sutured in position, or held in place by a single layer of gauze stuck to the surrounding skin by collodion. An elastic bandage and the air-inflatable spint are then applied over the gauze stent. The splint extends along the entire extremity, well beyond the graft area. The dressing is changed after 48 hours. If the splint remains in place for a much longer period, which at times is necessary, excessive moisture and even purulence may accumulate. To my knowledge neither the vinyl inflatable sheaths of Lehmann or Schwager et al, nor the inflatable rubber bags of Smith are in current use by plastic surgeons for skin grafting.

Accordingly there is a need for improved methods and apparatus for applying controllable pressure uniformly over the entire graft area, even where irregular in shape or elevation, which permits easy inspection of the graft while healing is in process, and reduces the adherence problem.

THE INVENTION

Objects

It is among the objects of this invention to provide an improved pressure pad for skin grafting and method of easily applying more nearly uniform pressure to grafted tissue during the healing or "taking" period.

It is another object to provide a transparent, fluid-filled skin graft pressure pad which permits continuous observation during healing without disturbing the pad or the graft tissue.

It is another object to provide a skin graft pressure pad that can be filled in any desired amount with a viscous clear fluid, the mass and fluid nature of which provides improved and uniform pressure over grafted tissue even on the margins and irregular areas, while the transparent nature of the pad permits visual examination or irradiation of the graft during healing.

It is another object to provide a means of (daily if necessary) injecting more fluid into the stent from time to time as required to increase pressure on the graft as necessary if and when the tie-down sutures loosen with time.

It is another object to provide a surface against which the skin graft will not adhere and thus not be torn, shredded or loosened while the stent is being removed.

It is another object to provide a controllably distensible bladder which will conform to a variety of differing shapes of the grafted area, thereby minimizing the need of manufacturing a large number of stents of differing sizes. p It is another object to provide a skin graft pressure pad specially adapted with means to permit air access to the graft tissue while healing.

It is another object to provide a skin graft pressure pad specially adapted with means for securing the pad in place over the grafted tissue area.

It is another object to provide a skin graft pressure pad that is sterilizable, reuseable, and rapid to apply.

Still further and other objects of this invention will be evident from the description which follows:

FIGURES

The description herein makes reference to the drawings in which.

SUMMARY

Figures 1, 2, 3, 4:
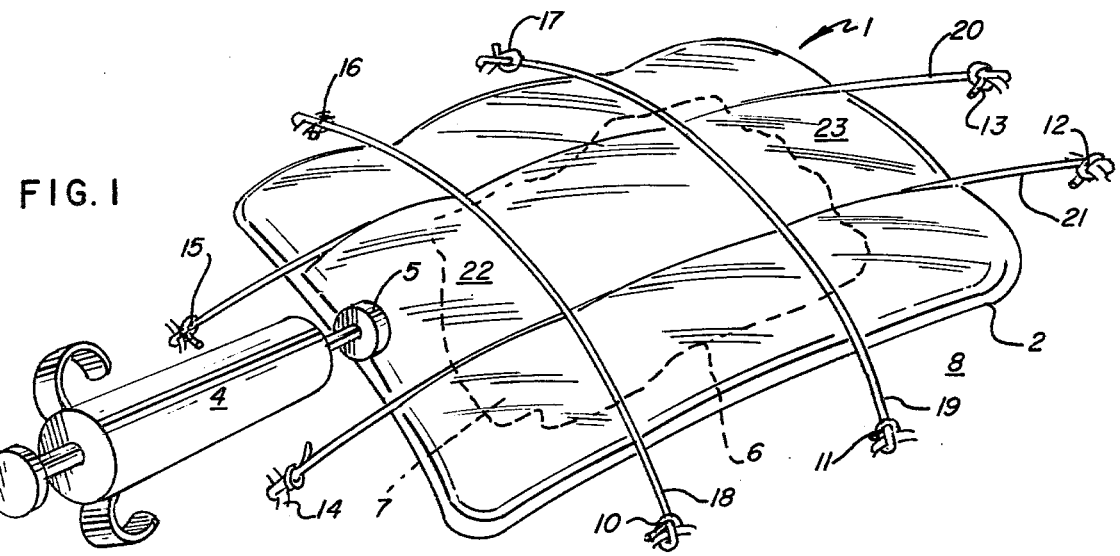
FIG. 1 is a perspective view of a first embodiment of the pressure pad of this invention in place over a grafted area illustrating the pad being able to be filled or emptied of the fluid filling, and employing a suture tie-over securing method.
FIG. 2 is a perspective view of another embodiment of the envention employing an open mesh border having adhesive on its skin-facing surface for securing the pad in place.
FIG. 3 is a section view of a pressure pad of the invention with a variety of securing means.
FIG. 4 is a section view of a pressure pad of this invention showing the graft-facing surface of the pad having a surface adapted to provide air passageways to the graft.

The pressure pads of this invention comprise a soft, easily deformable clear, transparent plastic bag or envelope retaining a clear, transparent liquid silicone filling material. The bag or envelope shape and size are preselected to be larger when filled than the area of the graft tissue so that pressure is applied by the bag uniformly across and to the edges of the graft. The transparency and clarity of the bag and liquid filling permits continuous inspection of the graft tissue during healing without removal of the pressure bag or disturbing the graft. The high viscosity and high index of refraction of the silicone (as compared to air), and generally oval cross sectional shape of the bag provides a degree of magnification of the graft tissue thereunder which aids inspection of the tissue. The clarity and transparency permit light, UV or IR irradiation of the graft tissue to promote healing.

The bag plastic is preferably of limited stretchability, and is of a material that has low adherability to graft tissue, insipated serous solutions, scab forming material and the like. A polyvinyl chloride or siloxane polymer film material is suitable. A filling port is provided in an upper or side bag surface. This permits controlled filling or evacuation of the bag contents with a syringe. In operation, the bag is preferably only partially filled, so that the bottom side will conform to the curve and shape of the graft tissue. The bag fill can be increased from time to time as necessary to maintain the proper pressure, e.g. where the securing means loosens.

The mass of the silicone filling material provides adequate grating pressure, and the precise total weight applied to the graft area can be controlled by adding or withdrawing silicone from the bag as desired. Overfilling is preferably avoided as this causes the bag to become more spherical, resulting in lifting the bag surface away from the edge of the graft area, and increasing undesirable lateral momentum upon body movements.

The viscous silicone filler provides an inertial function; the nature of the filling and the mass of the pressure pad is capable of absorbing blows, shocks and changes of direction which could cause slippage or shearing of the graft with respect to the base tissue. In addition, the mass of the bag serves both "alert" and "resistance" functions. The mass alerts or reminds the patient that the graft must be guarded. For example, for a graft on an extremity, the presence of the mass or weight sensed by the patient will tend to continuously make the patient more aware of the graft; the patient will move his or her limbs more carefully. The "resistance" function occurs by virtue of the patient having to lift or move the mass, which tends to make the patient move less, move more slowly, or lie quiet.

The bottom, or graft side, surface of the pad may be smoothly corrugated, quilted or otherwise configured to provide air or fluid passageways across the graft area from the edge of the pad.

The pad may be secured over the graft area by a variety of means and methods. In one embodiment, filaments may be sutured to the skin exteriorly of the graft area and passed over the bag to secure it in place. In another, preferred, embodiment, the bag includes one or more webs, flaps, strips or string-like ties extending from its periphery which permits removably securing the bag in position. These means can be tied together around a limb, or may be secured by adhesive tape, or themselves have one or more adhesive surfaces permitting adherence to the skin or others of the tie means.

DETAILED DESCRIPTION

This detailed description is by way of example and not by way of limitation of the principles of the invention.

FIG. 1 is an overall perspective of a principal embodiment of the invention in which pressure pad 1 comprises a plastic bag or outer envelope 2, partially filled with a viscous, transparent clear silicone 3. Syringe 4 permits filling or withdrawal of silicone through port 5. The bag assembly is shown of a size extending beyond the periphery 6 of skin graft area 7 on skin surface 8 of a patient 9. In this embodiment, the pad is held in place by a series of sutures 10, 11, 12, 13, 14, 15, 16, and 17 and filamentous-type tie-downs 18, 19, 20, and 21.

Note that due to the mass of the silicone, the bag is relatively thin. The bag is not over-filled with silicone, and accordingly conforms to the surface configuration of the grafted area. Due to the hydrostatic nature of the liquid silicone fill, the pressure transmitted to the graft tissue 7 by the tie-downs is distributed uniformly over the entire graft area.

Due to the clear transparent property of both the plastic envelope and the silicone fill, the graft tissue can be inspected, or it may be irradiated UV or other bacteria-deterring radiation. Convex regions such as 22, 23 are formed between adjacent tie-downs which provide a degree of magnification, assisting in the inspection.

There are several modes of application and use. A bag, prefilled with silicone may be applied to the graft area and then tied down, care being taken to properly tension all the ties. However, it is preferred to use a relatively empty bag, tie it down loosely, and then adjust to the proper tension by filling the bag with additional silicone introduced with the syringe 4 through port 5. In this manner, the ties need not be of precisely the same length or tension as the upper surface of the bag will conform (pillow-out) different amounts in different area, yet the hydrostatic pressure on the graft tissue will be substantially equally uniformly distributed. Also, the amount of fill in the bag can be increased from time to time, even daily, as the tie-overs or other securing means loosen.

The silicone also has the property of being warm to the touch. It stores heat from the body and can insulate the graft area. By the same token, as it is a heat sink, it can absorb and dissipate excess heat from inflamed tissue. The bag is very soft and pliable; being only partly filled, and having limited expansibility, it conforms well to complex surface shapes when placed thereon. After application, the stent of this invention is examined on a regular basis, e.g. daily rounds, and the fill adjusted to keep the pressure on the graft tissue adequate. Due to the transparency, the stent need not be disturbed to view the graft tissue. After the graft has taken, the stent can be removed, by cutting or loosening the tie-overs or other securing means, and gently pulling it away from the underlying tissue. Because of the nature of the envelope material, dried tissue, scab material, and serous fluids do not stick to it. The stent can be reused, after sterilization, or disposed-of.

FIG. 2 shows an alternative configuration of the bag and method of retaining it in position over the graft area. Pad 1 overlies the graft tissue 7 to generally extend beyond the edge of the graft 6 as shown by the dotted outline of the bag edge 24. The bag is secured in place with an expansible mesh 25 having opposed borders 26, 27 with pressure sensitive adhesive thereon. The mesh is gently expanded to size, placed over the bag and the adhesive borders 26, 27 pressed into place on the skin 8 of the patient 9. The port 5 is accessible through the openings in the mesh for filling or withdrawal of silicone 3 with syringe 4.

The central area of the mesh need not, but may also be adhesive coated so as to adhere to the upper surface of the bag. The apertures in the mesh permit inspection of the graft through the transparent bag envelope and silicone. A suitable mesh may be 3M "Steri-Strip" brand mesh skin closures. All materials adhering to skin tend to be insufficient for holding down a stent especially where surrounding areas are frequently in motion, e.g. the mandible or neck, or are covered by hair and/or sebaceous glands. Where sufficient surrounding skin is present, e.g. on the trunk or an extremity, a small (4 or 6 cm) stent may be held down using tincture benzoin and wide adhesive tape.

It should be understood that the port assembly 5 may be omitted from a pad, where adjustment of the pressure on the graft is not required or desired. When using mesh as described above, a portion of the mesh may be cut away to permit easier and larger access to the port. Because of the criss-crossed interlacing of the mesh, the overall structural integrity of the mesh is not lost, and suitable holding of the pad is provided. If more edge holding power is required, a double-sided pressure sensitive adhesive tape may be placed on the skin under the open mesh edges 29 and 30 of the mesh and the mesh pressed into place.

FIG. 3 is a perspective view, partly in section, of a pressure pad of the invention illustrating several alternative constructions.

In one alternative, pad 1 may have a solid, flexible plastic marginal flap 31, which may be continuous, partial or intermittent, around the periphery of the bag. Adhesive tape may be secured to this flap and thence to the patient's skin surface. This flap is preferably of sufficient thickness that sutures may be made through it into the patient's skin if desired. This flap preferably extends from the lower surface of the bag.

In another alternative, the marginal extension may be in the form of one or more strips 32 through 37. The strips may be plain as in 32 and 35, and of sufficient length to be tied together around a limb, such as an arm, or the body. Strips 33 and 36 have velcro type containing areas 38, 39 on the same, both or opposed sides (as shown) so they may be attached to each other or to another velcro area secured to the patient. Strips 34 and 37 have adhesive areas on opposed, the same (as shown), or both sides for securing the pad. Generally cylindrical ribs 55, spanning the interior of the pad between the top surface 53 and the bottom 42 may be employed to retain the pad in a thin lenticular or flat pancake shape.

FIG. 4 illustrates in section a pad 1 having a bottom surface 42 molded with corrugations 43 through 47 therein to provide passages 48 through 51. This permits drainage, irrigation, or air exposure to the graft tissue 7, to enhance it taking to the base tissue 52. The upper surface layer 53 of the bag is smooth in this embodiment. The graft tissue can be irrigated with medicament-containing solution, or drained of pus through these passages without disturbing the pad. The common contact area 54 is large due to the pliable nature of the bag, thus providing for adequate pressure on the graft tissue yet retaining adequate passageway size.

The bag plastic may be any suitable plastic polymer such as a transparent, limited and controllable expansibility, polyvinyl chloride or a siloxane polymer film, so long as the plastic is not substantially permeable to either tissue fluids, irrigation solutions or the fill liquid, and has low adherence to tissue and serous fluid. Typically the bag wall may range from 0.005 to 0.040" in thickness, but should be thin enough to be pliable as described above.

The fill is preferably a clear silicone fluid, preferably a dimethyl polysiloxane of formula

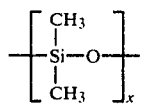

where x ranges from 2 to about 2,000, and having a viscosity on the order of from 0.65 to 12,000 centistokes. Most preferred is a silicone fluid having a viscosity from about 100 to 10,000 centistokes, and from 70 to 500 dimethyl polysiloxane units, and which may be partially cross-linked. For example, Dow Corning 360 Medical Fluid, or Dow Corning 382 Medical Grade Elastomer dimethyl polysiloxane fluids can be used. However, while medical grade silicone is preferred, it is not required as the pad is used external of the body.

Another silicone fluid may be a G.E. SF-96, SF-18 or VISCASIL dimethyl polysiloxane fluid having viscosities ranging from 5–2,000 (for SF-96), from 5,000–12,500 (for VISCASIL) and 350 (for SF-18), viscosity values in centistokes.

The viscosity of a silicone fluid can be precisely controlled by blending it with another viscosity grade of the same fluid to produce an intermediate viscosity.

As an alternative to silicone, water or water with a gelling agent, such as carboxymethyl cellulose, or a hydrolyzed 50/50 starch-polyacrylonitrile graft copolymer, may be used. One useful type of gelling agent is Flo-lok from Robinson Systems, the viscosity of which can be controlled by a degelling solution of common salt (NaCl) in water. In the case of the starch/acrylonitrile copolymer, the ratio of polymer gelling agent to water may be in the range of from 1/1000 to 1/3000 parts by weight. In any event, the viscosity may be adjusted in accord with the principles set forth herein.

Reference has been made throughout to "partial filling" of the bag, by which is meant that the bag contains less liquid fill than the maximum fully expanded bag volume, but the bag does not contain air in the unfilled volume. Rather, the bag surface may present a wrinkled appearance, which disappears when more liquid fill is added.

Pads may be any shape, typically varying from rectangular, to square, to oval, to round, to irregular. A useful type is round (in plan view) and sightly domed. A 4.2" (10.7 cm) diameter by 1" (2.5 cm) maximum thickness pad would typically weigh from about 100–150 grams (partly full); with one of 5.4" (13.6 cm) diameter by 1¼" (3.2 cm) thick pad weighing from about 200–250 grams (partly full). The pad weight can be reduced in each instance to 25–50 grams by withdrawal of fill, or increased to over 200 grams (in the first example), to over 300 grams (in the second example) by addition of fill.

Sterilization of the pad can be done by autoclaving, e.g. in a high speed flash sterilizer or standard gravity sterilizer. For high speed, the pad may be wrapped in a surgical towel and placed in a clean, open tray, then sterilized not less than 3 minutes at 270° F. (132° C.) at 30 psi (2 kg/cm$^2$). For the gravity method, the pad is wrapped as before and placed in the tray. Sterilization is for 30 minutes at 250° F. (121° C.) at 15 psi (1 kg/cm$^2$). Prevacuum sterilizers or ethylene oxide are not recommended as they may cause the liquid (water, gel or silicone) to bubble, or residual ethylene oxide may cause adverse reaction in the sensitive graft tissue or base tissue.

It should be understood that various modifications within the scope of this invention can be made by one of ordinary skill in the art without departing from the spirit thereof. I therefore wish my invention to be defined by the scope of the appended claims as broadly as the prior art will permit, and in view of this specification if need be.

I claim:

1. A skin graft pressure pad comprising in operative combination:
   (a) means defining an enclosure for a liquid mass comprising a soft, easily deformable, transparent plastic bag and having a property of low adherence to tissue or serous fluids on at least one skin graft contact surface thereof;
   (b) said enclosure means being pliable, freely conformable to variations in surface contour, and non-freestanding;
   (c) at least one substantially transparent liquid disposed in said enclosure in an amount to at least partially fill said enclosure to permit said free surface conformability;
   (d) the volume of said enclosure and amount of said liquid being selectable to provide mass sufficient to enhance growth-promoting contact between grafted tissue and underlying tissue without substantial tissue necrosis;
   (e) means for removably securing said enclosure containing said liquid in contact with said graft tissue; and
   (f) said securing means being adapted to retain said pad in a predetermined position in direct continuous contact with said graft tissue to permit said liquid to transmit substantially uniform, growth-promoting pressure to said graft tissue without inducing substantial tissue necrosis.

2. A pressure pad as in claim 1 wherein said securing means comprises a plurality of flexible members disposed to permit visual observation of at least a portion of said graft tissue through said enclosure and said liquid.

3. Pressure pad as in claim 2 wherein said flexible members comprise a mesh.

4. A pressure pad as in claim 2 wherein said flexible members comprise filamentous tie-downs adapted to be secured to sutures.

5. Pressure pad as in claim 2 wherein said flexible members comprise flexible strips.

6. Pressure pad as in claim 1 which includes a web extending from the margin of said pad along at least a portion of the periphery of said pad.

7. Pressure pad as in claim 1 which includes at least one port for introduction or withdrawal of said liquid thereby permitting control of the mass of said pad.

8. Pressure pad as in claim 1 wherein the surface of said enclosure placed adjacent said graft is adapted to provide passages for fluid.

9. Pressure pad as in claim 1 wherein said liquid is selected from a silicone fluid, water, and water having a gelling agent therein, the viscosity of said liquid ranging from about 1 to 12,000 centistokes.

10. Pressure pad as in claim 9 wherein said liquid has a viscosity in the range of from about 100 to 10,000 centistokes.

11. Pressure pad as in claim 10 wherein said liquid is a dimethyl polysiloxane silicone fluid.

12. Method of applying uniform pressure to a skin graft comprising the steps of:
   (a) selecting a partially full, liquid-containing pressure pad having a graft-tissue-facing surface larger than the area of said graft, said pressure pad comprising a soft, easily deformable, non-freestanding transparent plastic bag, and having a property of low adherence to tissue and serous fluids on at least one skin graft contact surface thereof;
   (b) applying said pressure pad in free surface conformability to said area;
   (c) maintaining said pad in direct continuous contact with said graft tissue with removable securing means; and
   (d) maintaining the pressure pad of said pad on said graft area by adjusting the tightness of said securing means relative to the amount of said liquid in said pad;
   thereby transmitting uniform pressure sufficient to promote contact between said graft tissue and underlying base tissue without substantial necrosis of said tissues.

13. Method as in claim 12 wherein said step of maintaining the pressure of said pad includes controlling the volume of liquid in said pad after said pad is secured in place, said controlling is selected from introducing and withdrawing liquid from said pad by a syringe means.

14. Method as in claim 12 which includes the step of inspecting the progress of the taking of said graft by viewing the graft tissue through said pad.

15. Method as in claim 12 which includes the step of irrigating said graft tissue with a fluid introduced in spaces provided between said pad and an upper surface of said graft tissue.

16. Method as in claim 12 wherein said step of maintaining said pad in place includes providing sutures in skin tissue to which said pad is secured.

17. Method as in claim 12 wherein said step of maintaining the pressure of said pad includes selecting the fluid in said pad to permit said pad to freely conform to irregularities of contour in said skin surface.

18. Method as in claim 17 wherein said step of fluid selection includes controlling the viscosity of said fluid in the range of from 1–12,000 centistokes.

19. Method as in claim 18 wherein said viscosity is controlled in the range of from 100 to 10,000 centistokes.

* * * * *